US00PP12032P2

(12) United States Plant Patent
Hines

(10) Patent No.: US PP12,032 P2
(45) Date of Patent: Aug. 7, 2001

(54) MAGNOLIA GRANDIFLORA NAMED 'HALEHINES01'

(76) Inventor: Terry D. Hines, 710 Hines La., McMinnville, TN (US) 37110

( * ) Notice: Subject to any disclaimer, the term of this patent is extended or adjusted under 35 U.S.C. 154(b) by 0 days.

(21) Appl. No.: 09/305,257

(22) Filed: May 4, 1999

(51) Int. Cl.[7] ..... A01H 5/00

(52) U.S. Cl. ..... Plt./223
(58) Field of Search ..... Plt./223

*Primary Examiner*—Bruce R. Campell
*Assistant Examiner*—June Hwu
(74) *Attorney, Agent, or Firm*—Klarquist Sparkman Campbell Leigh & Whinston LLP

(57) ABSTRACT

A new variety of *Magnolia grandiflora* 'Halehines01' is characterized by a slow growth rate and compact habit with dense green foliage.

2 Drawing Sheets

The present invention relates to a new and distinct variety of *Magnolia grandiflora*, commonly called Southern Magnolia. I have given my plant the varietal name 'Halehines01'.

Southern Magnolias are typically extremely variable in growth habit, leaf and flowering characteristics. Seedling grown material is often open and unkempt. These characteristics typically limit the attractiveness of the plants in landscaping applications.

It is not unusual for Southern Magnolia trees to grow from one to two feet per year. For example, Southern Magnolia trees growing in the same block and which were the same age as the parent tree of my new variety at the time it was discovered were about five to seven feet tall at about four years of age.

U.S. Plant Pat. No. 9,243 relates to a Southern Magnolia tree named 'MGTIG'. This tree is a rapidly growing Southern Magnolia tree with the patent referring to three year old plants growing in a nursery in Monroe, Ga. having a typical height of seven to eight feet and a width of four feet. The 'MGTIG' trees are described as having a dense framework of branches and leaves. The rapid growth of the 'MGTIG' variety makes it less desirable in landscaping applications where a slower growing, smaller tree is preferred.

With this as background, the parent tree of my new variety of Southern Magnolia tree was discovered in the spring of 1996 growing in a cultivated area of a nursery in Warren County, Tenn. I was attracted to my new tree by its small size and dense foliage. At the time, my new tree and other Southern Magnolia trees growing in the same block were about four years old. However, my new tree was only about twenty-four inches tall, while the other Southern Magnolia trees growing in the block were from about five to seven feet tall.

Asexual reproduction of the new variety at my direction from cuttings has been accomplished at the Hale & Hines Nursery in Warren County, Tenn. Observations of the resulting progeny growing in this nursery has proven the characteristics of my new variety to be fixed. Furthermore, these observations have confirmed that my new variety represents a new and improved variety of Southern Magnolia tree, as particularly evidenced by the following unique combination of characteristics, which have proven firmly fixed, are outstanding therein, and which distinguish it from all of the varieties of this species of which I am aware:

1. A small, slow-growing shrub-like tree; and
2. Very dense green foliage.

OVERALL DESCRIPTION OF THE VARIETY

'Halehines01' is an attractive plant that exhibits a slow growth rate compared to other varieties of Southern Magnolia trees. Observations of Southern Magnolia trees of my new variety maintained in a test block of plants under standard outdoor nursery conditions of normal water and fertilizer have confirmed that these plants have growth rates of from about six to about eight inches per year. In addition, internode lengths of about three-fourths inch to one inch (about 1.5 to 2.5 centimeters) have been observed in these trees, which results in leaves of the trees being densely clustered in a compact growth habit. The trees attain a small shrubby appearance which is broadly pyramidal in habit.

My new plant has not yet been observed to bloom so that flower shape, size, color, petal shape, petal flowering, stamen color, and fragrance are all unknown.

The leaves of my new plant have been observed to be about four to five inches long (about 10 to 12 centimeters) and about one and one-fourth inch to one and three-fouth inches wide (about 3 to 4 centimeters wide). The leaves are thick and firm and lanceolate to elliptic in shape, glossy above and smooth beneath, and are green to yellow-green color at maturity.

My new variety has been asexually reproduced by cuttings that may be planted using standard methods, such as placing the cuttings in horticultural grade perlite in four inch deep flats on a greenhouse bench under an intermittent mist. All plants of my new variety which have been asexually propagated have been identical, insofar as observable, to the parent plant.

BRIEF DESCRIPTION OF THE DRAWING

The accompanying photographs depict the color, leaf size, and growth habit of *Magnolia grandiflora* 'Halehines01'.

DETAILED BOTANICAL DESCRIPTION

Figure 1:
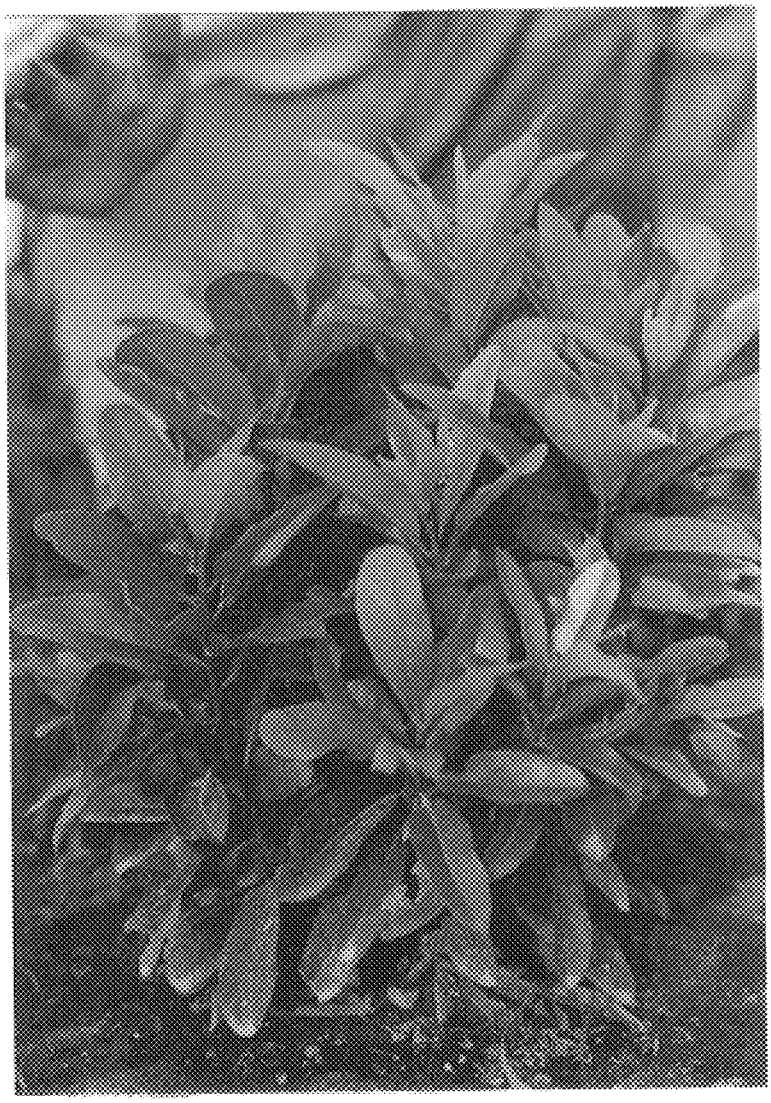
FIG. 1 is a photograph of the parent plant two years after it was inadvertently cut-back to a stump and shows the overall growth habit of the tree.
Figure 2:
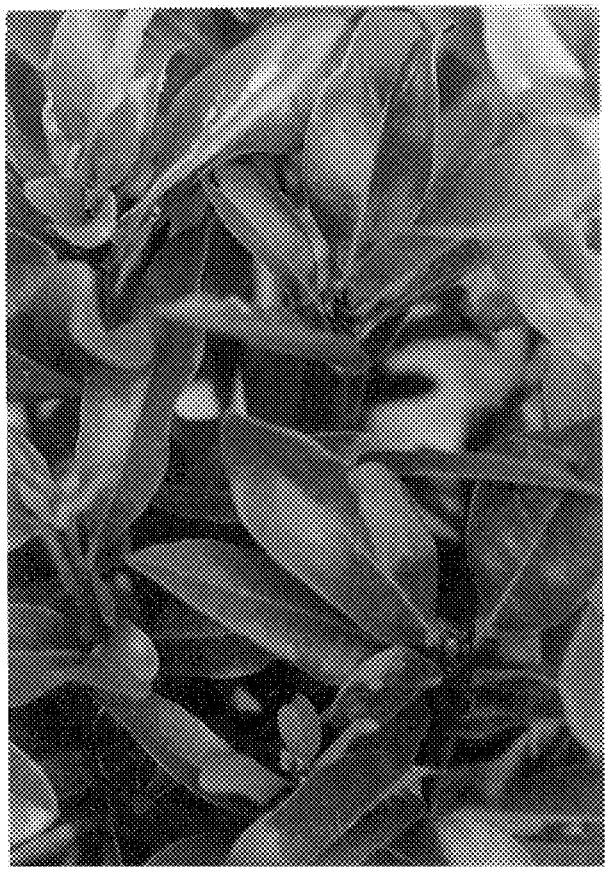
FIG. 2 is a close-up photograph of foliage of my new variety of plant showing leaf shape, color and internode length.
Figure 3:
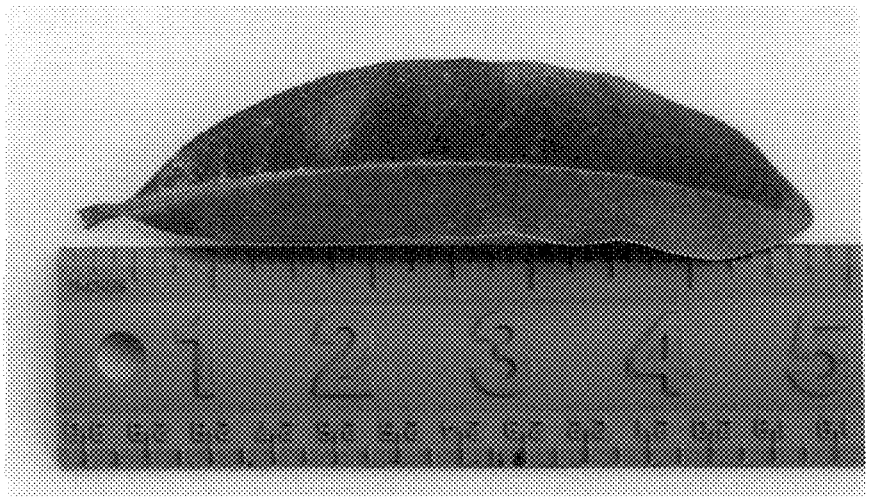
FIG. 3 is a photograph of an individual leaf depicting the leaf size in relation to a scale.

The following is a detailed description of my new variety of Southern Magnolia tree, with color terminology in accordance with The Royal Horticultural Society Colour Chart (hereinafter R.H.S.), published by The Royal Horticultural Society of London.

Parentage: Seedling of unknown parentage.

Propagation: Holds to distinguishing characteristics through succeeding propagations by rooted cuttings.

Locality where grown and observed: Warren County, Tenn.

Tree: Strong and stocky upright shrub-like tree with a compact, broadly pyamidal habit. The plant has a straight single leader with secondary branches that ascend at an angle of about thirty degrees from the leader. Internode length ranges from about three-fourths inch to one inch (about 1.5 to 2.5 centimeters) resulting in a dense foliage canopy.

Branches:

*Strength*.—First year stems are less stout than typical of the species and average about one-fourth inch to about three-eighths inch in diameter. Branches are smooth.

*Pubescent*.—New stems and buds are covered with present, fine, rusty-brown pubescence that disappears with maturity. Second year and older stems are completely glabrous.

*Color*.—First year stems are yellow-green (like R.H.S. 146B), second year stems are yellow-green (like R.H.S. 146A), and third year stems develop a grey-brown color (like R.H.S. 199C) and a smooth bark.

Vigor: Slower growing than other varieties of Southern Magnolia trees. Progeny of my new variety growing in Lucedale, Miss. under outdoor nursery conditions in containers have been observed to grow an average of about six to eight inches in height per year.

Foliage:

*Size*.—Leaves average about four to five inches (about 10 to 12 centimeters) long and about one and one-quarter inch to one and three-fourths inch (about 3 to 4 centimeters) wide.

*Shape*.—The mature leaves are lanceolate to elliptic in overall shape, are cuneate at their base, have an apex which is acute to blunt, and a margin which is entire.

*Venation*.—Pinnate — has been added.

*General character*.—Thick and firm but less coriaceous than species, glossy above and lack glossiness below. Alternate along the lower branches and tends to be clustered or whorled along the upper portion of the branches.

*Color*.—The upper leaf surface, adaxial is a lustrous green (like R.H.S. 147A) and a low leaf surface about abaxial is a yellow-green (like R.H.S. 146B).

*Petiole*.—Stout, average about 0.4 inch (about 1 centimeter) long. The petioles are a yellow-green (like R.H.S. 151B).

*Pubescent*.—Mature leaves are glabrous, the green color of the leaves is maintained throughout the seasons due to the absence of brown pubescence on the underside of the leaves.

Flowers and fruits: None observed to date.

Ultimate tree size: Unknown at this time, although original tree at four years of age was about twenty-four inches high (this tree was cut back).

*Pest resistance*.—Pest free, as typical for *Magnolia grandiflora*.

*Cold hardiness*.—Survived at temperatures at least as low as 10° Fahrenheit.

I claim:

1. A new and distinct variety of *Magnolia grandiflora* tree named 'Halehines01' substantially as herein shown and described.

* * * * *

UNITED STATES PATENT AND TRADEMARK OFFICE

CERTIFICATE OF CORRECTION

PATENT NO. : PP 12,032 P2
DATED : August 7, 2001
INVENTOR(S) : Terry Hines

It is certified that error appears in the above-identified patent and that said Letters Patent is hereby corrected as shown below:

Column 4,
Line 10, the phrase "has been added" should be deleted.
Lines 17-18, the words "low leaf surface about abaxial" should read -- lower leaf surface, abaxial --.

Signed and Sealed this

Seventh Day of May, 2002

*Attest:*

*Attesting Officer*

JAMES E. ROGAN
*Director of the United States Patent and Trademark Office*